(12) United States Patent
Crockford

(10) Patent No.: US 7,040,156 B2
(45) Date of Patent: May 9, 2006

(54) FLEXIBLE MEMBRANE ENCAPSULATED STRAIN MEASUREMENT INSTRUMENT AND METHOD OF MANUFACTURE

(76) Inventor: William Crockford, 13066 S. Dowling Rd., College Station, TX (US) 77845

( * ) Notice: Subject to any disclaimer, the term of this patent is extended or adjusted under 35 U.S.C. 154(b) by 0 days.

(21) Appl. No.: 10/647,844

(22) Filed: Aug. 21, 2003

(65) Prior Publication Data
US 2005/0039540 A1    Feb. 24, 2005

(51) Int. Cl.
*E21B 47/06* (2006.01)
(52) U.S. Cl. .................................... 73/152.52
(58) Field of Classification Search ............... 73/784, 73/152.01–152.18, 152.51, 152.52
See application file for complete search history.

(56) References Cited

U.S. PATENT DOCUMENTS

| | | | |
|---|---|---|---|
| 3,992,928 A * | 11/1976 | Thoms | 73/784 |
| 4,542,655 A * | 9/1985 | Park et al. | 73/784 |
| 4,579,003 A | 4/1986 | Riley | |
| 4,734,649 A * | 3/1988 | Barnaby | 324/376 |
| 4,989,452 A * | 2/1991 | Toon et al. | 73/293 |
| 5,025,668 A | 6/1991 | Sarda et al. | |
| 5,540,101 A * | 7/1996 | Capelle et al. | 73/784 |
| 6,084,052 A * | 7/2000 | Aufdermarsh et al. | 73/152.01 |
| 6,417,540 B1 * | 7/2002 | Sugihara et al. | 257/316 |
| 6,591,690 B1 | 7/2003 | Crockford | |

* cited by examiner

*Primary Examiner*—Max Noori
(74) *Attorney, Agent, or Firm*—McHale & Slavin PA

(57) ABSTRACT

A flexible membrane for use in test cells includes instrumentation within the thickness of the membrane to accurately measure a property of a material including stresses, strains, deformation, temperature, moisture potential and moisture content of the sample. A test sample is enclosed within the membrane to isolate the specimen from testing fluids in the test chamber. The instrumentation may measure axial strains or radial strains or both.

16 Claims, 11 Drawing Sheets

FLEXIBLE MEMBRANE ENCAPSULATED STRAIN MEASUREMENT INSTRUMENT AND METHOD OF MANUFACTURE

RELATED APPLICATIONS

This application is related to U.S. application Ser. No. 09/715,371 to Crockford which is incorporated herein by reference.

FIELD OF THE INVENTION

This invention relates to the field of testing equipment and, particularly, to test cells for soil samples.

BACKGROUND OF THE INVENTION

Geotechnical and paving materials such as soil and asphalt are often tested to obtain their engineering properties in axisymmetric triaxial testing cells. The specimen shape is usually a solid right circular cylinder. In rare cases, a hollow cylinder is used. The triaxial cells allow simultaneous pressurizing of the specimen periphery and deviatoric stress loading in one or more directions, usually the axial direction. The pressurizing media include a range of fluids such as air, mineral oil, or water though other fluids may be employed.

Since the test specimens are porous in nature, and the porosity is often structured such that the specimen is permeable to the pressurizing medium therefore, it is necessary to introduce an impermeable seal around the specimen to isolate the mechanical effect of confining stress. In order to allow the specimen to change shape during testing, this impermeable seal must be flexible, usually made of polymers such as latex, nitrile or silicone for testing paving materials and soils, while it may be a metal (e.g. copper) jacket for testing solid rock.

Displacement measurement(s) are usually necessary for computing the desired engineering properties from the stresses and strains (engineering strain is related to displacement through a very simple equation). It is often impossible to use the traditional resistance strain gauge in this application because (a) the specimen sometimes cannot be instrumented with a strain gauge that relies on adhesives, (b) large strains are difficult to precisely measure with typical resistance strain gauges, and (c) the surface void texture causes the strain gauge to be inaccurate. The axis of the cylinder is usually vertical, so the deviatoric loading and the related strains are parallel to this axis. Therefore, the vertical displacement measurements are required for all but the most basic engineering properties e.g., simple material strength does not require the measurement of strain, it only requires measurement of stress. Vertical strains combined with horizontal strains can be used for determining Poisson's ratio and dilation parameters.

The horizontal or radial strain may be measured at a number of points on the surface of the cylinder, or by one or more circumferential measurements which has the advantage of reducing the number of transducers and improving the signal to noise ratio of a given transducer, if it is an analog device, or by other means such as volume change or optical measurements.

U.S. Pat. No. 5,025,668 issued to Sarda et al. has instrumentation which is externally referenced. Such an apparatus has limitations: (1) it is not immune from end effects, and (2) it does not uncouple the vertical from the horizontal displacement. End effects alter strain measurements from the true value because the specimen deforms more like a whiskey barrel than like a right circular cylinder. The end effects are worse (a) when the friction between the specimen end and the loading platen is high, as is the case with many soils and virtually all asphalt materials, (b) when the measurement is taken with a gauge length that spans the whole specimen height from end to end, (c) when the specimen is short, and (d) when the properties at the ends of the specimen are different from the true properties of the specimen in the middle portion of the specimen for example, molded specimens tend to have somewhat different densities and air void properties close to the ends. The end effects often affect the vertical strain measurements more than the radial measurements.

If radial measurements are taken, they should be uncoupled from the vertical movement. Since the radial measurements are usually very small in relation to the vertical on materials having Poisson's ratio smaller than 0.5, friction at the end of the shaft in contact with the specimen can introduce bending and/or binding in the shaft, causing the measured radial deflection to be incorrect.

U.S. Pat. No. 4,579,003 issued to Riley also illustrates instrumentation that is externally referenced. Riley discloses an improvement over the device disclosed by Sarda in that the instrumentation is internal to the triaxial cell, but it is still external to the specimen. At the very small displacements commonly measured with soils and asphalt, any interface between any material other than the material being tested and some other material, such as a metal or polymer platen, can cause enough deformation under load to totally mask the correct strain measurement. Therefore, measuring between the stages as disclosed by Riley is likely to produce better measurements than Sarda's device.

SUMMARY OF THE INVENTION

Disclosed is a flexible membrane for use in test cells to measure a property of a material including stress, strain, temperature, deformation, moisture content, etc. The test cells include instrumentation within the thickness of the membrane to accurately measure stresses causing deformation of the sample. A test specimen may be enclosed within the membrane to isolate the specimen from testing fluids in the test chamber. The instrumentation may measure axial stresses and strains or radial stresses and strains or a combination thereof.

U.S. patent application Ser. No. 09/715,371 submitted by the Applicant and incorporated herein by reference, notes several instrumentation means. When mounting of the instrumentation is done by mechanically attaching to the membrane, moment analyses are useful as described in the application. While moment analyses are always useful, in the particular case of an application in which the vertical displacement measurement means is either (a) the only measurement means, or (b) is capable of being completely separated from the radial measurement means in a combined measurement configuration, it is possible to make an even simpler instrumentation means by making the instrumentation an integral part of the membrane.

Therefore, it is an objective of this invention to provide a flexible membrane for intimate contact with the surface of the specimen to isolate the specimen from the testing fluids in the test cell and permit the specimen to deform in response to testing stresses.

It is another objective of this invention to provide instrumentation integrally incorporated within the membrane to quantify and record the strains.

It is yet another objective of this invention to provide an instrumented membrane to measure radial or axial strains, alone.

It is a further objective of this invention to provide instrumentation to measure axial and radial stresses. The circumferential approach would be the most appropriate method for measuring radial properties using the instrumentation and one skilled in the field will be able to extend the teaching directed toward the vertical measurement presented herein to include both the vertical and the horizontal or only the horizontal in various embodiments.

It is still another objective of this invention to provide instrumentation in the membrane to measure the temperature, moisture content and/or soil suction of a specimen during a test.

Other objectives and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

DETAILED DESCRIPTION OF THE INVENTION

Figure 1:
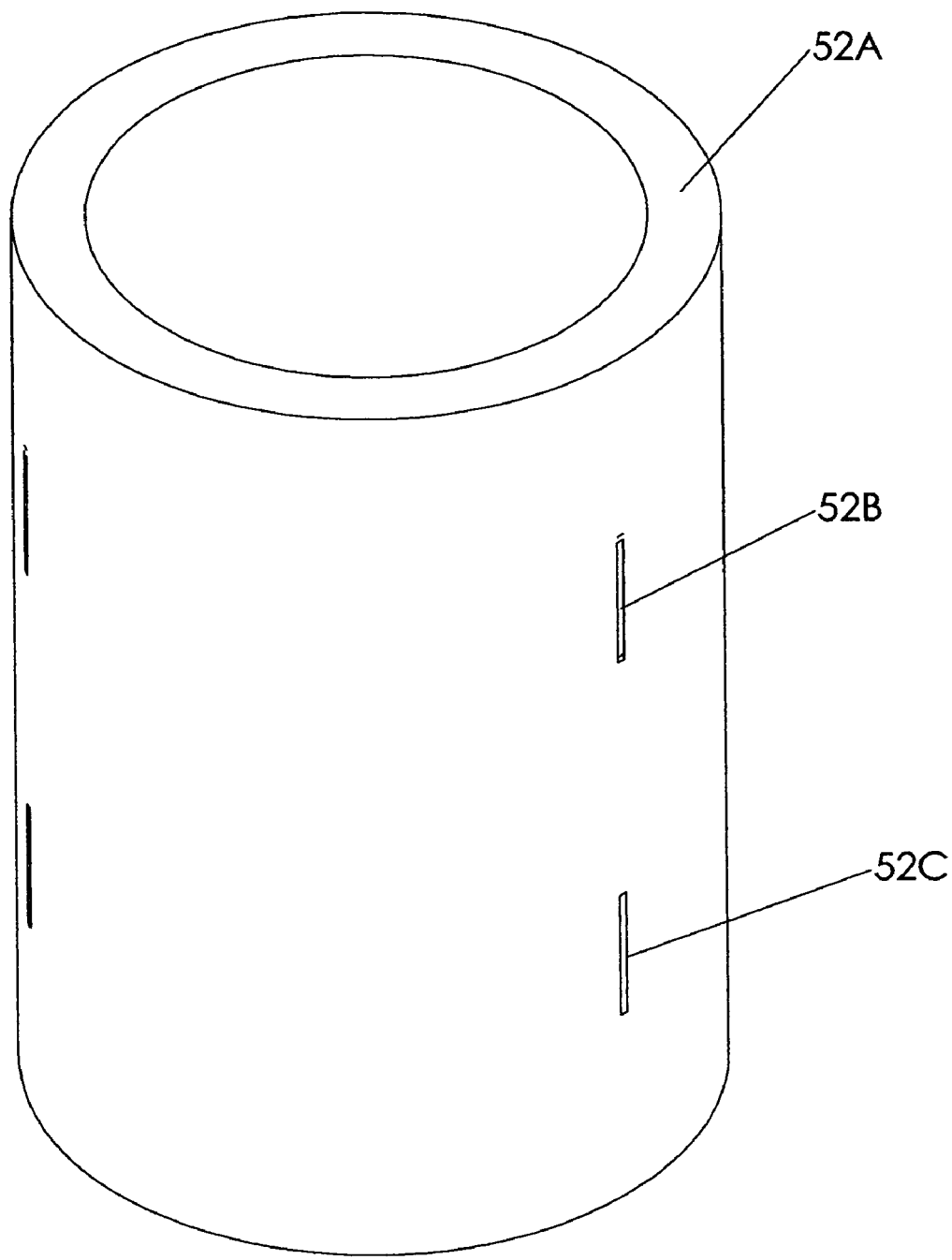
FIG. 1 is a perspective view of instrumented membrane for axial measurements only.
Figure 2:
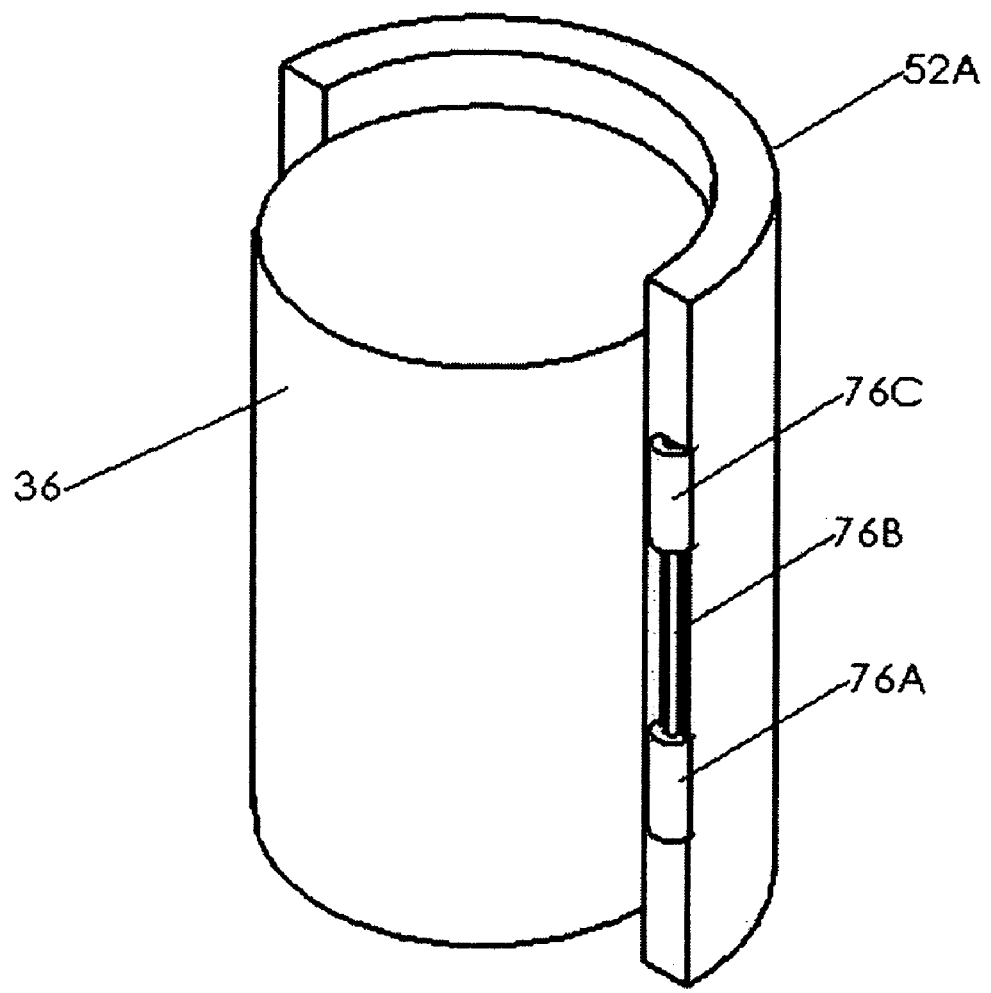
FIG. 2 is a partial section view of instrumented membrane for axial measurements only with a specimen in place.

FIG. 1 shows the straight tube portion 52A of the membrane and FIG. 2 shows a section view through the membrane and one of the vertical measurement instruments. FIG. 2 also shows a specimen 36 to be tested in the axial direction. In a constant thickness version of the membrane, the thickness of 52A in FIG. 1 is thicker than the cross section dimension of the displacement sensor, which requires its minimum thickness to be larger than that necessary to produce the pressure barrier alone. The thickness may vary in other embodiments, such as that produced by the fabrication mold assembly, discussed below in the manufacturing method portion of this application. The membrane section shown in FIGS. 1 and 2 show a cavity 52B that is molded into the membrane material, such as silicone or latex rubber, or other polymeric materials, and this cavity receives the LVDT (linear variable differential transformer) type displacement transducer. The cavity 52B is tubular in nature in nature, but it is not centered within the wall thickness of the membrane. By offsetting the cavity toward the outside surface of the membrane, the large diameter portions of the cavity are actually open to the outside surface of the membrane by the slit 52C in FIG. 1.

The inside diameter of the membrane is, therefore, continuous so that no leakage of the pressurizing fluid occurs from one side of the membrane to the other. Although the outside slits are provided to make it possible to insert the parts of the transducer into the cavity after the membrane has been molded, it would be possible to mold the transducer into the rubber during manufacture. However, there are wires that come into an LVDT type device that are not shown at 76A, and these wires may make membrane manufacture with the transducer in place during the manufacturing somewhat cumbersome. Further, individual molded-in transducers, even if they were wireless, would be difficult to replace without destroying the membrane. Of course, the instrumented membranes may be a single use type or capable of multiple tests. In the preferred embodiment, the LVDT type sensor would be placed in the cavity after the membrane has been manufactured.

Figure 8:
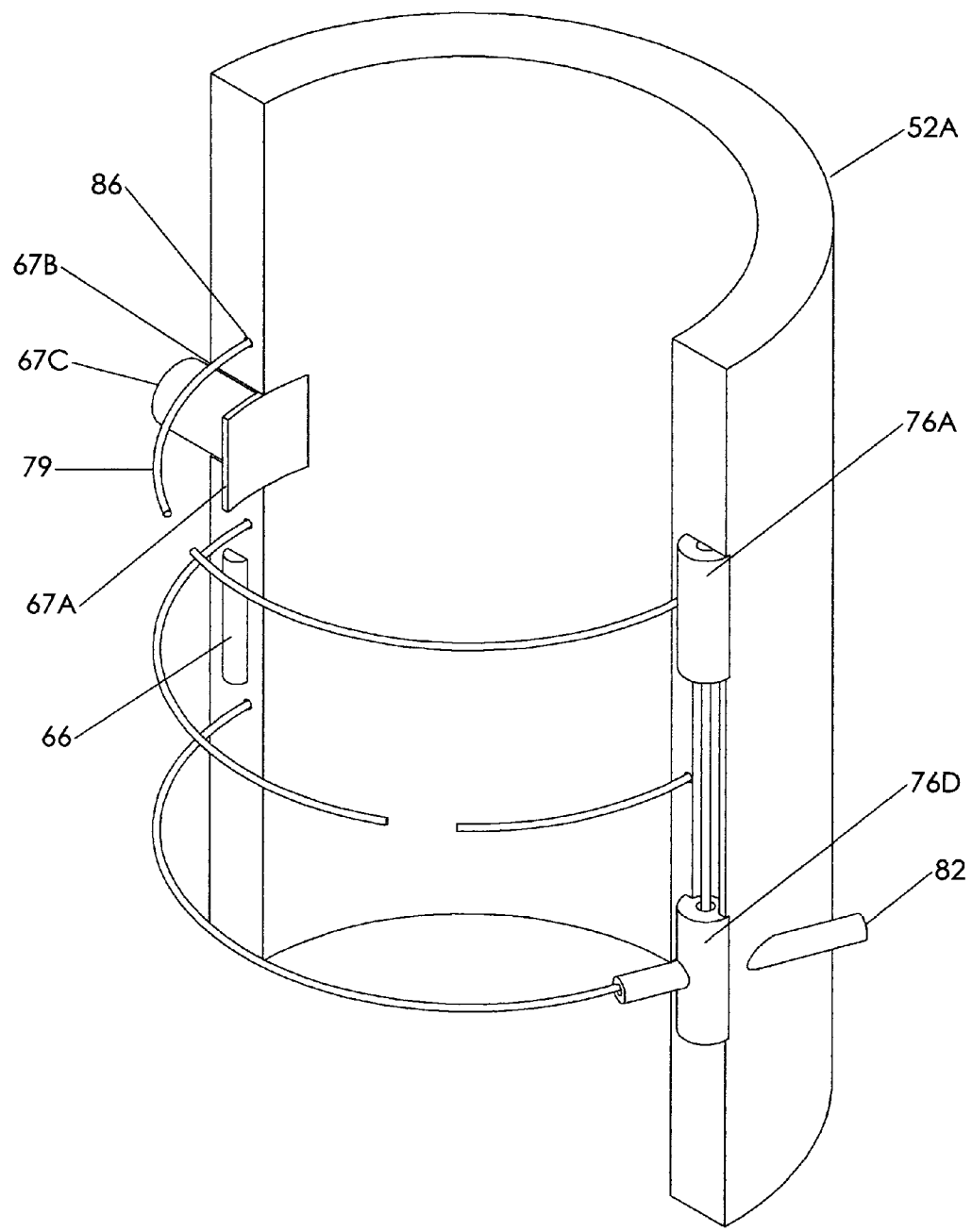
FIG. 8 is a perspective of an alternate embodiment of the membrane for combination measurements with a temperature probe and moisture content chamber.

The temperature probe 66 may also be molded in the membrane, as well as, the screen 67A of the moisture content chamber 67B, shown in FIG. 8. The moisture content chamber 67B may have an instrument 67C therein which measures soil suction or soil potential. A source of these dielectric probes or tensiometers is Soilmoisture Equipment Corp in California.

The screen 67A may be a semipermeable membrane to maintain isolation of the sample from the testing fluid or in the event the walls of the moisture content chamber 67B are made impervious the screen 67A may be a sieve.

The LVDT type sensor usually comprises three or more parts: a transformer body 76A, a core and core rod extension 76B and a piece of anchoring hardware 76C used in conjunction with the core rod extension to establish the desired gauge length for the measurement. Since these three components can be separated, and since the membrane is usually a flexible elastomer such as a silicone or latex rubber or a cast urethane, it is possible to (a) insert the body of the LVDT into the upper or lower slit 52C in the membrane and allow the wires to hang out of the slit, and (b) insert the other components into the other slit in the membrane. Once in place, the friction between the inside surface of the membrane and the outside diameter of the specimen under test will allow measurement of the vertical deflection of the specimen under load. The changing distance between 76C and 76A when the specimen experiences strain due to the axial load generates a measurable displacement signal.

The preferred embodiment would use multiple sets of vertical LVDTs for example, three sets of parts 76A, 76B, and 76C arranged in a pattern at 120 degree angle increments about the central axis of a cylindrical specimen, although fewer or more LVDTs would be possible. Four sets would be preferred, if the specimen were rectangular instead of cylindrical.

Figure 3:
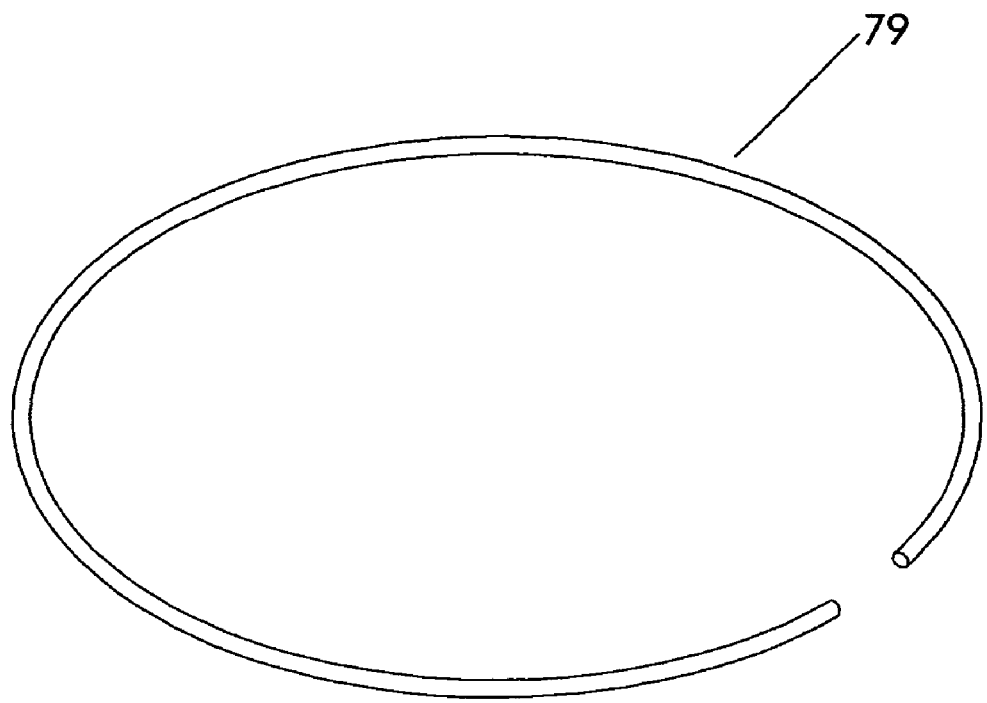
FIG. 3 is a perspective of the flexible cord.
Figure 4:
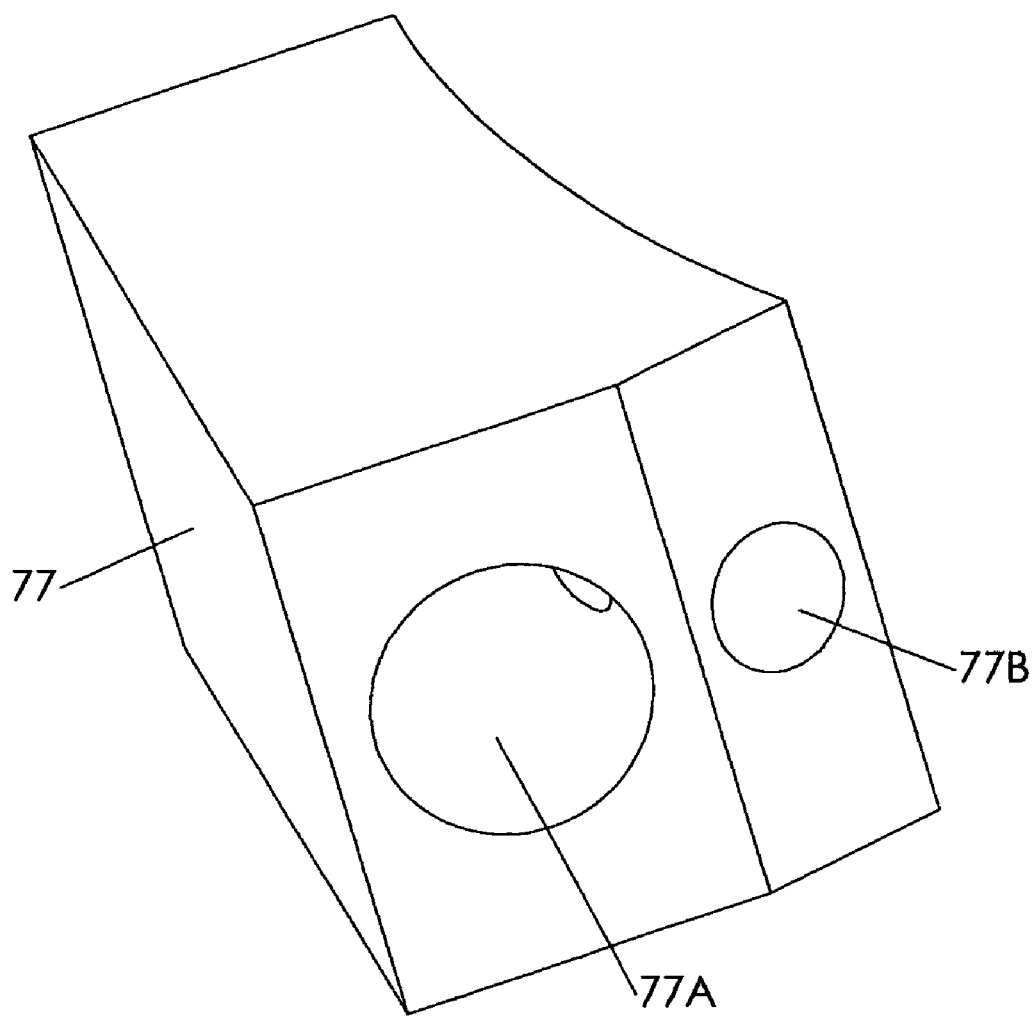
FIG. 4 is a perspective of the mounting hardware for independent circumferential measurement.
Figure 5:
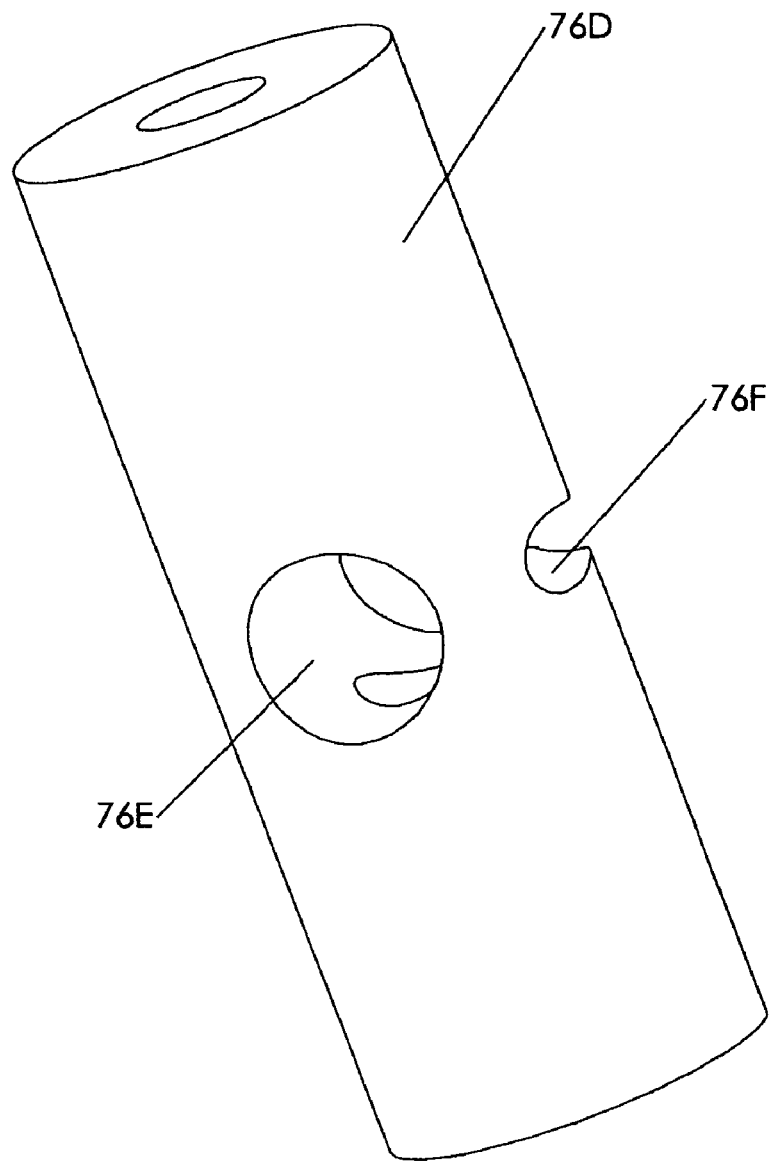
FIG. 5 is a perspective of the mounting hardware for combination vertical and circumferential measurement.
Figure 6:
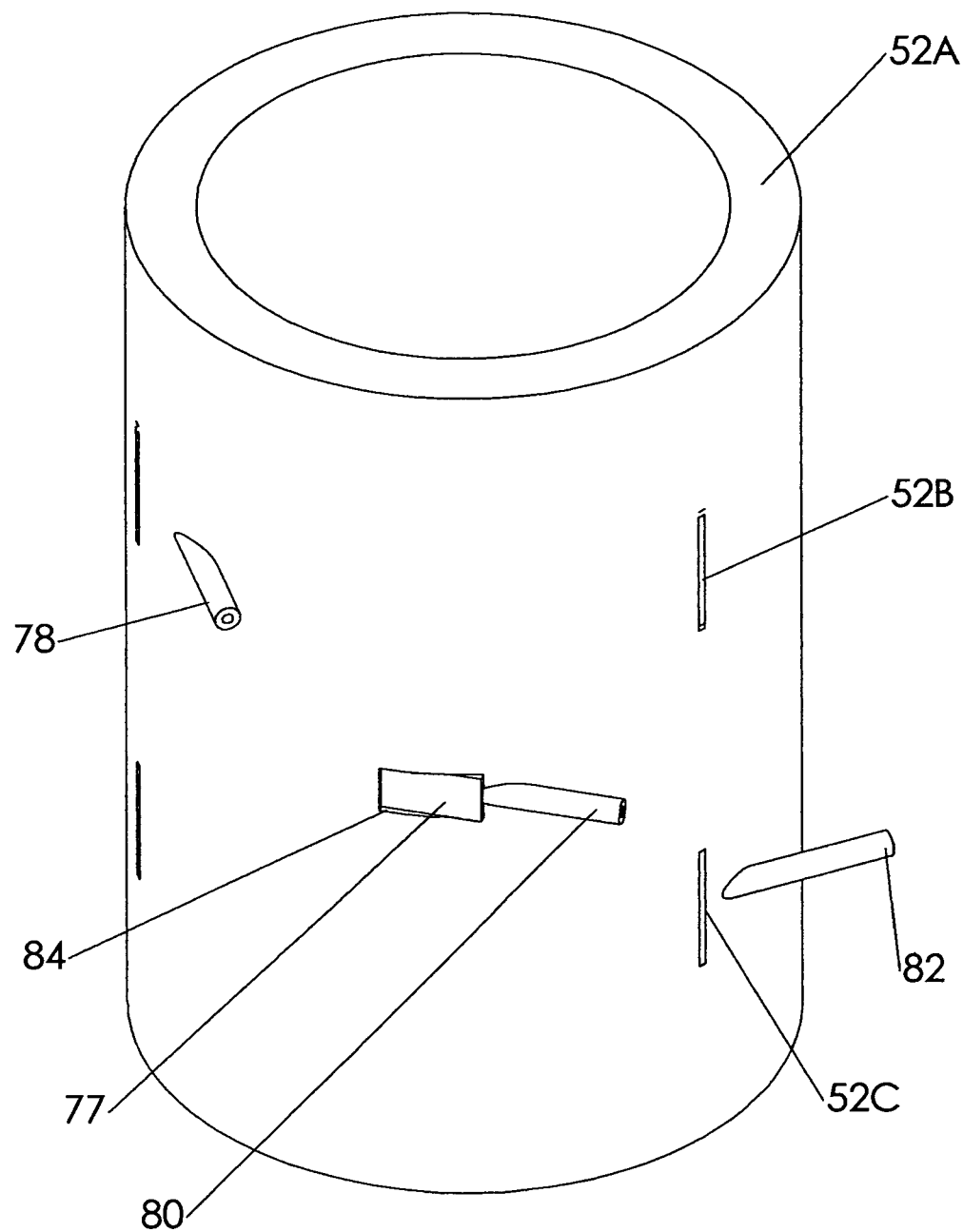
FIG. 6 is a perspective view of instrumented membrane for combination axial and circumferential measurements.

In order to measure radial strain using a circumferential measurement on a cylindrical specimen, the preferred embodiment comprises a flexible cord or ribbon 79 shown in FIG. 3, mounting hardware 77 shown in FIG. 4, or 76D shown in FIG. 5, and a spring-loaded LVDT 78, 80, and/or 82, shown in FIG. 6. Mounting hardware 77 would be mounted in an additional membrane cavity 84. The flexible cord may be of any cross sectional shape. If the available clearance space is very small, flat or oblong shapes may be improvements over circular cross sections to reduce stress on the membrane.

Figure 7:
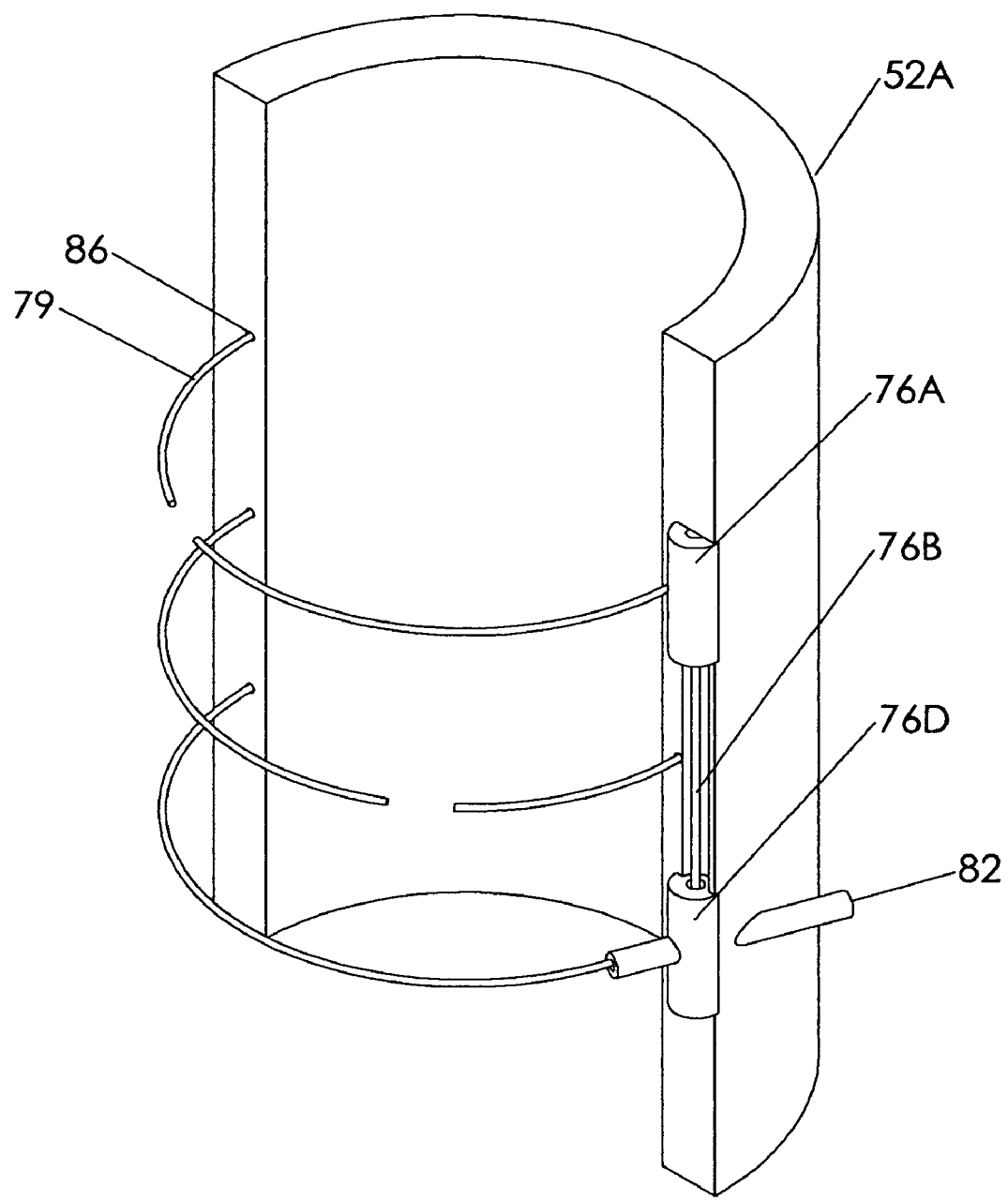
FIG. 7 is a partial section view of instrumented membrane for combination axial and circumferential measurements.

For a single radial measurement, the preferred embodiment would position the circumferential measurement components at the mid location, as shown by LVDT 80. As shown in FIG. 7, this flexible cord should pass freely through a cavity 86 in the membrane that is closer to the inside surface of the membrane than the core rod 76B. In FIG. 4, LVDT 80 would be mounted in the larger of the two holes 77A in the mount 77, one end of the flexible cord would be attached to the LVDT and the other end of the cord would be attached in the smaller hole 77B using an adhesive. The two holes in the mounting hardware 77 should be fabricated at an angle that will allow the two ends of the flexible cord that are attached at the LVDT and at 77B to maintain tangency to the circle they define in the membrane cavity as closely as possible.

For two radial measurements, one embodiment would comprise two such component assemblies positioned above and below the mid-height at some distance that would give a representative picture of the radial deformation if it were to deform in a barrel shape instead of a perfect right circular cylinder. In the preferred embodiment, using either two or three radial measurements, the vertical anchor hardware 76C could be modified to perform double duty as a combination radial LVDT holder and anchor for the vertical LVDT 76D. Using the double duty configuration along with the mid-height mount enables three radial measurements to be taken that can be averaged or used independently to better quantify the overall shape during deformation. The combination unit 76D, incorporates features additional to the basic features that comprise the standard anchor unit 76C, including a mounting feature such as a hole 76E to receive the spring-loaded radial LVDT, and a notch 76F. The notch 76F is used to anchor one end of the cord 79 for example, with an adhesive or by crimping, in the anchor that also has the LVDT mounted in it. At other locations around the 120 degree pattern, the notch is simply a clearance notch that allows the cord 79 to pass through unobstructed.

Figure 9:
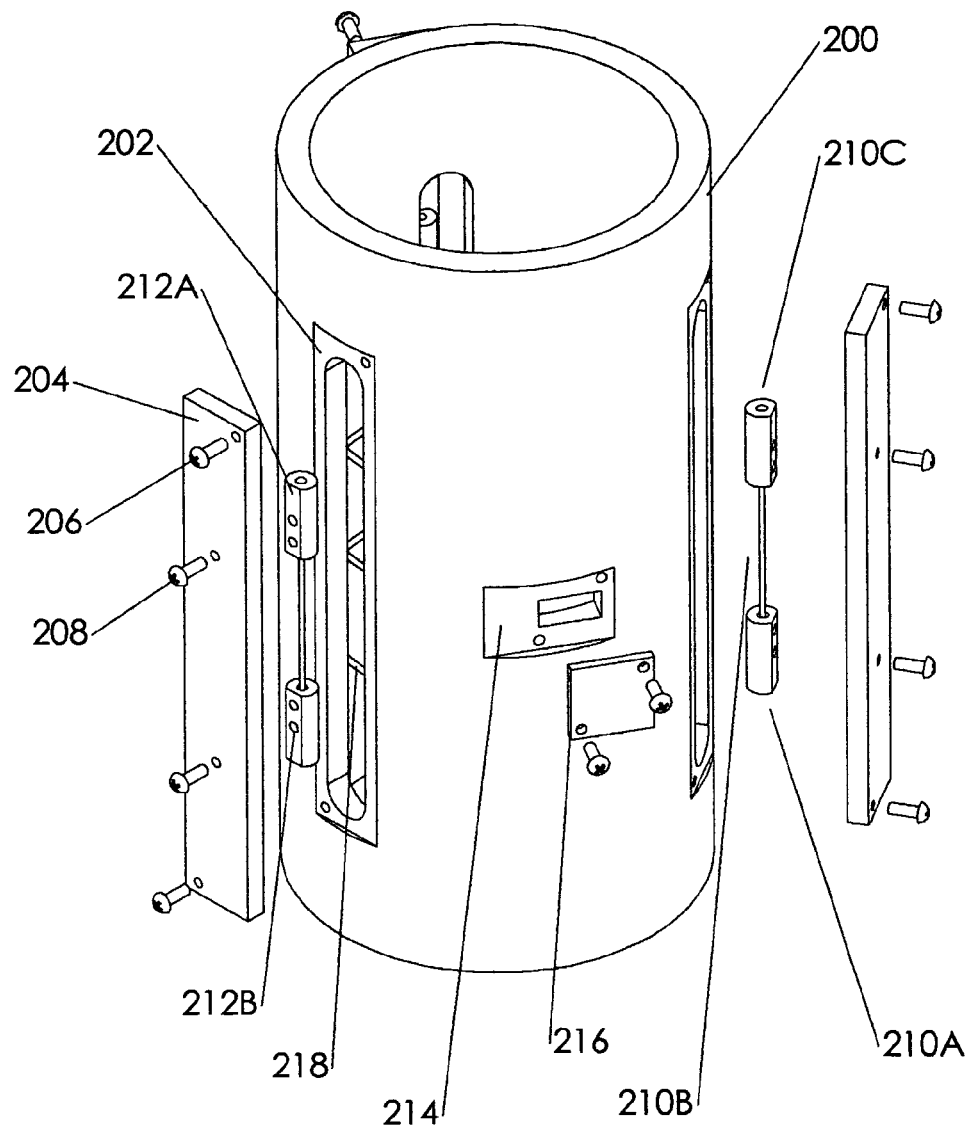
FIG. 9 is an exploded view of membrane manufacturing mold.

While there are various sophisticated methods of forming polymers, a very simple method of manufacturing membranes with cavities is illustrated in FIG. 9. When assembled, the device illustrated in FIG. 9 is filled with an appropriate quantity of raw membrane material, closed on the ends, and inserted into a device that can be rotated around the central axis, such as a lathe. The centrifugal force during rotation will generate an evenly distributed layer of material on the inside of the tube, simultaneously filling the areas around the LVDT cavities.

Various flexible materials can be used, and a chemical mold release agent may or may not be necessary to enable release of the cured membrane material from the mold surfaces. Dow Corning's two part Silastic material has been found suitable for a membrane material. This material cures faster under heat which allows reduction of the time necessary to rotate the mold.

In FIG. 9, the mold tube 200 has an inside diameter that is determined by the specimen diameter and the desired membrane thickness. The outside diameter of the tube is determined by the diameter of the measurement device. One or more flats 202 are fabricated on the outer diameter of the mold. A mold plate 204 will be attached to the mold flats with plate attachment screws 206 after the instrument cavity components 210A, 2108, and 210C have been attached to the plate with instrument cavity mold screws 208.

The instrument cavity components 210A, 210B, and 210C are dimensionally designed to receive the instrument components 76A, 768, and 76C. Instrument cavity shaft 210B must be larger in diameter than instrument shaft 76B because the instrument shaft must be free to move in the cavity without friction. Leakage of the pressurizing medium through the slits 52C allows for pressure relief/equalization in the shaft cavity so that it neither appreciably inflates nor collapses on the instrument shaft during pressurization. The lower and upper mold body components 210A and 210C are preferably designed with slightly smaller dimensions than the corresponding instrument parts 76A and 76C so that the instrument components will be tightly held in the cavity of the finished membrane. The instrument cavity components 210A and 210C have a flat 212A fabricated on them and one or more threaded holes 212B on the flat. Cavities for different gauge lengths can be attained by attaching to the different mounting holes as desired.

For applications only requiring vertical (i.e. axial) measurements, features 214, 216, and 218 are unnecessary. For a single circumferential measurement, and for applications in which radial measurements do not occupy the same horizontal planes occupied by the vertical cavity components 210A and 210C, a support 216 having a cavity 216A by a wire 218 such as used to form the cavity 86 are used.

For applications only requiring vertical (i.e. axial) measurements, and for applications in which radial measurements do not occupy the same horizontal planes occupied by the cavity components 210A and 210C, those components can be of the same design as shown in FIG. 9.

Figure 10:
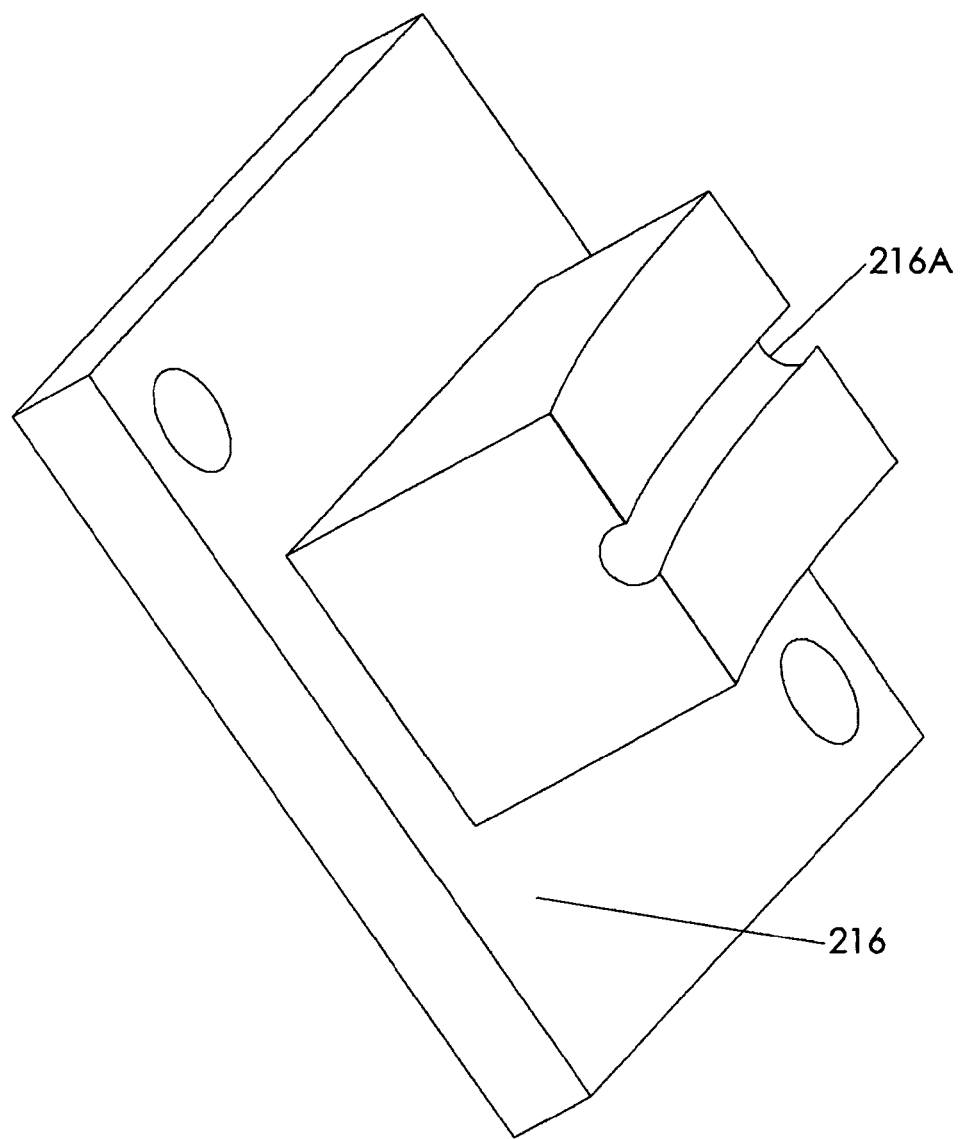
FIG. 10 is a perspective of the circumferential measurement mounting hardware.
Figure 11:
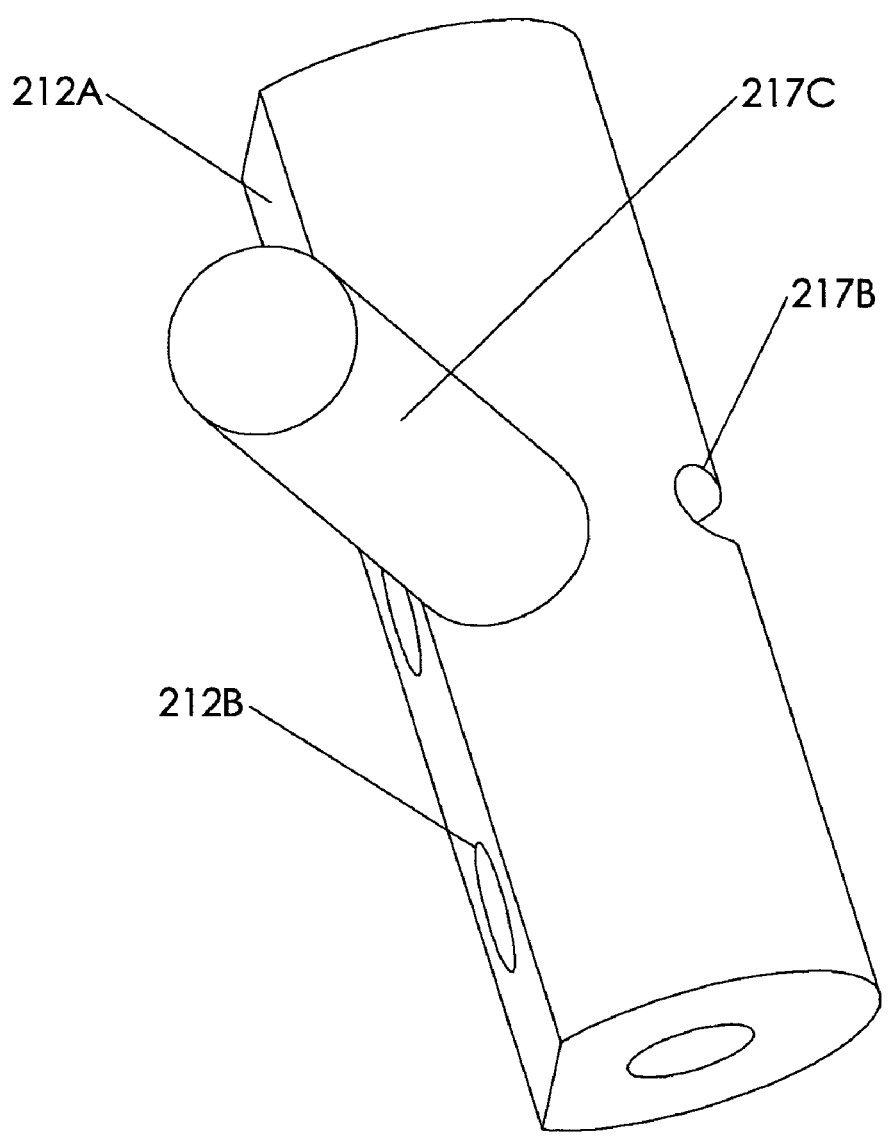
FIG. 11 is a perspective of an alternate embodiment of mold hardware for circumferential measurement capability.

For multiple circumferential measurements that require the use of mounting hardware 76D, in FIG. 5, the corresponding mold components require the additional support features 217B and/or 217C, in FIG. 10, of another embodiment. The extrusion or boss 217C is required only at those positions that require a circumferential instrument for example, 78 and 82, and a vertical anchor at the same location. The notch 217B is required at all positions for which the wire 218 needs to be supported on a vertical mold body component. As an example, for the case of the lower wire 218 located in the plane occupied by component 210A, one mold component located at 210A would need both the notch 217B and the boss 217C.

The configuration of the other two vertical mold body components located around the 120 degree pattern would only require the notch 217B in order to ensure that the wire 218 remains in a level plane perpendicular to the axis of the cylinder during the molding process and would therefore not require the boss.

A number of embodiments of the present invention have been described. Nevertheless, it will be understood that various modifications may be made without departing from the spirit and scope of the invention. Accordingly, it is to be understood that the invention is not to be limited by the specific illustrated embodiment but only by the scope of the appended claims.

What is claimed is:

1. A membrane for use inside a testing cell, which cell has a pressure chamber for receiving a specimen and applying forces to said specimen, said membrane comprising a flexible film adapted to envelope said specimen and isolate said specimen from the interior of said pressure chamber, said membrane adapted to maintain intimate contact with said specimen, instrumentation embedded in said membrane for measuring a physical property of a specimen.

2. A membrane of claim 1 wherein said physical property being one of the group consisting of stresses, strains, deformation, temperature, soil suction or moisture content.

3. A membrane of claim 1 wherein said membrane has a longitudinal axis and a radial axis, said instrumentation oriented in said membrane to measure said physical property in the longitudinal direction.

4. A membrane of claim 1 wherein said membrane is tubular, said instrumentation oriented in said membrane to measure said physical property in the circumferential direction.

5. A membrane of claim 4 wherein said membrane has a longitudinal axis and a radial axis, said instrumentation oriented in said membrane to measure said property in the longitudinal direction.

6. A membrane for use in a testing cell to isolate a specimen, said membrane comprising a flexible film having a thickness, said membrane adapted to enclose a specimen, instrumentation embedded in said membrane for measuring a physical property of a specimen wherein said instrumentation is oriented in multiple directions in said membrane to measure said physical property and calculate Poisson's ratio.

7. A membrane of claim 1 wherein instrumentation is embedded in said membrane for measuring strains causing deformation of a specimen.

8. A membrane of claim 7 wherein said membrane has a longitudinal axis and a radial axis, said instrumentation oriented in said membrane to measure strains in the longitudinal direction.

9. A membrane of claim 7 wherein said membrane is tubular, said instrumentation oriented in said membrane to measure circumferential properties in response to stresses.

10. A membrane of claim 9 wherein said membrane has a longitudinal axis and a radial axis, said instrumentation oriented in said membrane to measure strains in the longitudinal direction.

11. A membrane for use in a testing cell to isolate a specimen, said membrane comprising a flexible film having a thickness, said membrane adapted to envelope a specimen, instrumentation embedded in said membrane for measuring strains causing deformation of a specimen wherein said instrumentation is oriented in multiple directions in said membrane to measure said physical property and calculate Poisson's ratio.

12. A membrane of claim 7 wherein said instrumentation includes an instrument for measuring temperature in the specimen.

13. A membrane of claim 7 wherein said instrumentation includes an instrument for measuring moisture content of the specimen.

14. The membrane of claim 7 wherein said instrumentation includes an instrument for measuring soil potential.

15. A membrane of claim 1 wherein said flexible film is formed from one of the group consisting of latex rubber, silicone rubber, urethane, or Silastic.

16. A membrane of claim 1 wherein said flexible film is tubular with a continuous sidewall with a cavity formed in said sidewall, said instrumentation disposed in said cavity.

* * * * *